United States Patent [19]

Philippossian et al.

[11] 4,299,833
[45] Nov. 10, 1981

[54] 1-ISOPROPYL- AND 1-ISOBUTYL-3,7-DIMETHYL XANTHINE AS MEDICAMENTS

[75] Inventors: Georges Philippossian, Lausanne; Marc Enslen, Yverdon, both of Switzerland

[73] Assignee: Societe d'Assistance Technique Pour Produits Nestle S.A., Lausanne, Switzerland

[21] Appl. No.: 148,044

[22] Filed: May 8, 1980

[30] Foreign Application Priority Data

May 22, 1979 [CH] Switzerland .......................... 4780/79

[51] Int. Cl.$^3$ ............................................. A61K 31/52
[52] U.S. Cl. ..................................... 424/253; 544/267
[58] Field of Search .......................... 424/253; 544/267

[56] References Cited

FOREIGN PATENT DOCUMENTS 4780 6/1979 Switzerland .

OTHER PUBLICATIONS

C. A. 40, (1946), 3185[5], Abstract of J. Pharmacol. 86, 113-119, (1946).
C. A. 42, (1948), 985[f], Abstract of J. Pharmacol. Exptl. Therap. 91, 288-291, (1947).

Primary Examiner—Frank Cacciapaglia, Jr.
Attorney, Agent, or Firm—Vogt & O'Donnell

[57] ABSTRACT

The invention relates to 1-isopropyl- and 1-isobutyl-3,7-dimethyl xanthines as medicaments. They have a sedative effect comparable with that of a standard neuroleptic.

2 Claims, No Drawings

1-ISOPROPYL- AND 1-ISOBUTYL-3,7-DIMETHYL XANTHINE AS MEDICAMENTS

This invention relates to 1-isopropyl- and 1-isobutyl-3,7-dimethyl xanthine as medicaments.

The known pharmacological properties of xanthines are their stimulating effect on the central nervous system, their spasmolytic activity and their diuretic activity.

Behavioural studies on rats have unexpectedly shown that, in contrast to the psychostimulating xanthines used for therapeutic purposes, such as for examples caffeine or theophylline, 1-isopropyl-3,7-dimethyl xanthine and 1-isobutyl-3,7-dimethyl xanthine have a sedative effect comparable with that of a standard neuroleptic, such as chlorpromazine and haloperidol.

Accordingly, the present invention relates to a pharmaceutical composition containing 1-isopropyl- or 1-isobutyl-3,7-dimethyl xanthine in combination with an inert pharmaceutically acceptable carrier or support. The pharmaceutical composition contains an active quantity for the neuroleptic effect of the active material.

The active substances 1-isopropyl- and 1-isobutyl-3,7-dimethyl xanthine are prepared by N-alkylation in position 1 of theobromine by phase transfer catalysis according to the process described in Swiss Patent application No. 4780/79-6 which corresponds to U.S. application Ser. No. 148,045, filed May 8, 1980, now abandoned, and which is incorporated by reference in the present application as if it were set forth at length.

The medicaments according to the invention may be made up in various pharmaceutical forms containing the usual excipients or vehicles, such as tablets, capsules, suppositories, solutions, suspensions, and may be administered orally, sublingually, rectally, subcutaneously, intramuscularly, intravenously or by inhalation, in daily doses of from 0.02 to 0.2 g.

The compounds have an acute toxicity in mice of from 200 to 300 mg/kg when administered orally and from 100 to 200 mg/kg when administered intraperitoneally.

The invention is illustrated by the following Example

EXAMPLE 1-isopropyl- and 1-isobutyl-3,7-dimethyl xanthine were the subject of a behavioural study on rats as a function of the anxiety induced by a new environment. Rats show their anxiety by rising up on their two rear paws, whilst their movements express locomotive activity.

Method

An anxiety state is induced by confronting "naive" male Sprague-Dawley rats (Iffa-Credo, France) weighing from 260 to 300 g with a new environment in the form of cages of Macrolon (30×25 cm) which are situated in a soundproofed and air-conditioned chamber (22° C./50% relative humidity).

The number of rearings and movements is determined automatically from infra-red photoelectric cells which only emit electrical pulses for the complete movements of the animal and not for static movements, like those of the head and tail, for reasons of reproducibility. These photoelectric cells sweep the cages at two different levels so as to distinguish the rearings from the movements. The number of rearings and movements is countered by the two groups of photoelectric cells, memorised and then printed out according to a pre-established programme.

The compound under test is orally administered in solution by oesophageal intubation, the reference administration being formed by 6 ml/kg of distilled water, 30 minutes before the animals are placed in the cages. The number of rearings and movements is determined during the 15 minutes following encagement in relation to the effect produced by the reference administration.
Evaluation of the results Table 1 below showed the development of the effects of the tested substances on the number of displacements and rearings in dependence upon the doses administered expressed as a percentage of the displacements and rearings counted for the reference administration.

TABLE 1

| Substance | Dose administered mg/kg oral | Movements % of the reference administration | Rearings % of the reference administration |
| --- | --- | --- | --- |
| 1-isobutyl-3,7-dimethyl xanthine | 7.5 | 107 | 95 |
| | 10 | 87 | 74 |
| | 12.5 | 82 | 72 |
| | 15 | 64 | 56 |
| | 17.5 | 55 | 46 |
| | 20 | 49 | 35 |
| 1-isopropyl-3,7-dimethyl xanthine | 10 | 92 | 89 |
| | 20 | 81 | 80 |
| | 30 | 85 | 64 |
| | 40 | 56 | 36 |
| | 50 | 42 | 24 |
| chlorpromazine | 5 | 109 | 105 |
| | 7.5 | 80 | 90 |
| | 10 | 62 | 70 |
| haloperidol | 0.16 | 104 | 120 |
| | 0.31 | 73 | 73 |
| | 0.63 | 63 | 57 |
| | 0.94 | 52 | 51 |
| | 1.25 | 43 | 40 |
| | 1.56 | 37 | 29 |
| | 2.5 | 6 | 5 |
| chlordiazepoxide | 5 | 85 | 85 |
| | 7.5 | 85 | 72 |
| | 10 | 69 | 57 |
| | 12.5 | 58 | 44 |

From the preceding data, the regression lines for the movements and rearings are established by the method described by Saubrie, P. J. Pharmacol (Paris) 2 (1971) 457–472, the equation of these regression lines corresponding to the average expressed in % of the performances of the controls in dependence upon the product of multiplication by 10 of the logarithm of the doses (only the doses which do not reduce the motive activity by more than 75% are considered).

The gradients of the regression lines corresponding to the movements and to the rearings are compared by recording on the abscissa (d) of a system of orthogonal axes the value of the gradient of the line representing the movements and, on the ordinate (r), the value of the gradient of the line representing the rearings. These values demonstrate the effect-dose relation for a given substance.

The ratio of the gradient of the movements to that of the rearings is also determined, enabling the specificity of the effect of a given substance on the anxiety state to be judged.

The results obtained are set out in Table II below:

TABLE II

| | Movements | Rearings regression |
| --- | --- | --- |

TABLE II-continued

| Substance | regression line | gradient ≠ 0 | line |
|---|---|---|---|
| 1-isobutyl-3,7-dimethyl-xanthine | y = −138.7 x+ 367.5 | P<0.001 | y = 135.9 x+ 350.7 |

| | | gradient ≠ 0 | Comparison of the gradients $(d/r)$ |
|---|---|---|---|
| 1-isopropyl-3,7 dimethyl-xanthine | y = −43.32 x+ 186.5 | P<0.001 P<0.05 | N.S. y = 69.75 x+ 225 P<0.05 $(d/r < 1)$ |
| chlor-promazine | y = −84.58 x+ 238.6 | P<0.05 P<0.05 | y = 0.67.11 x+ 211.6 N.S. |
| haloperidol | y = −51.99 x+ 100.9 | P<0.01 P<0.01 | y = 59.2 x+ 103.9 N.S. |
| chlordiaze-poxide | y = 66.72 x+ 202.4 | P<0.01 P<0.01 | y = −108.3 x+ 273.2 P<0.01 $(d/r < 1)$ |
| theophylline | y = 40.54 x+ 61.83 | P<0.001 N.S. | y = −9.63 x+ 119 P<0.001 $(d/r > 1)$ |

Legend:
- comparison of the gradients is carried out by the "t" test to the probabilities P 0.05, P 0.01 and P 0.001.
- N.S. means that the gradient is not significantly different from 0 or that the ratio between the gradients of the movements and the rearings is not significantly different from 1.

Conclusions

The effect of a substance is determined by its localisation in relation to the line d=r of gradient=1. The substances situated on this line have a similar effect on the rearings and movements. The substances for which the absolute value of the gradient of the rearings is significantly higher than that of the movements have a specific effect on anxiety.

Table II above shows:
that 1-isobutyl-3,7-dimethyl xanthine has an action profile similar to the neuroleptics chlorpromazine and haloperidol, i.e. it is non-specific sedative; that 1-isopropyl-3,7-dimethyl xanthine has a slightly anxiolytic sedative effect of the type developed by chlordiazepoxide; that theophylline is a psychostimulant and does not have any effect on anxiety.

We claim
1. A pharmaceutical composition containing an effective quantity of 1-isopropyl-3,7-dimethyl xanthine in combination with an inert pharmaceutically acceptable carrier to produce a neuroleptic effect.
2. A pharmaceutical composition containing an effective quantity of 1-isobutyl-3,7-dimethyl xanthine in combination with an inert pharmaceutically acceptable carrier to produce a neuroleptic effect.

* * * * *

UNITED STATES PATENT AND TRADEMARK OFFICE
CERTIFICATE OF CORRECTION

PATENT NO. : 4,299,833                      Page 1 of 2

DATED : November 10, 1981

INVENTOR(S) : Georges Philippossian and Marc Enslen

It is certified that error appears in the above—identified patent and that said Letters Patent is hereby corrected as shown below:

Columns 2 and 3, Table II, second heading should read:
--Movements
regression line--;

fourth heading should read:
--Rearings
regression line--.

Column 3, lines 10-12 of Table II should be considered in conjunction with the Substance "1-isobutyl-3,7-dimethyl xanthine" and the horizontal line appearing at line 12 should be deleted.

Table II at Column 3, under the second heading "regression line", the second entry thereunder, "-43.32" should read -- -48.32 --.

UNITED STATES PATENT AND TRADEMARK OFFICE
CERTIFICATE OF CORRECTION

PATENT NO. : 4,299,833

DATED : November 10, 1981

INVENTOR(S) : Georges Philippossian and Marc Enslen

It is certified that error appears in the above—identified patent and that said Letters Patent is hereby corrected as shown below:

Table II at Column 3, under the fourth heading "line", the second entry thereunder "69.75" should read -- -69.75 --.

Table II at Column 3, under the fourth heading "line", the fourth entry thereunder "59.2" should read -- -59.2 --.

Table II at Column 3, under the second heading "regression line", the fifth entry thereunder "66.72" should read -- -66.72 --.

Signed and Sealed this

Ninth Day of February 1982

[SEAL]

Attest:

Attesting Officer

GERALD J. MOSSINGHOFF

Commissioner of Patents and Trademarks